(12) United States Patent
Sasaki

(10) Patent No.: US 8,353,818 B1
(45) Date of Patent: Jan. 15, 2013

(54) ENDOSCOPE TRACKING SYSTEM AND METHOD

(76) Inventor: Larry Sasaki, Shreveport, LA (US)

( * ) Notice: Subject to any disclaimer, the term of this patent is extended or adjusted under 35 U.S.C. 154(b) by 187 days.

(21) Appl. No.: 12/802,310

(22) Filed: Jun. 3, 2010

Related U.S. Application Data

(60) Provisional application No. 61/217,672, filed on Jun. 3, 2009.

(51) Int. Cl.
*A61B 1/04* (2006.01)

(52) U.S. Cl. ............ 600/117; 600/101; 604/500; 396/17

(58) Field of Classification Search .................. 600/101, 600/117; 396/17
See application file for complete search history.

(56) References Cited

U.S. PATENT DOCUMENTS

| | | | |
|---|---|---|---|
| 5,671,739 A * | 9/1997 | Darrow et al. ................. | 600/424 |
| 2007/0197896 A1* | 8/2007 | Moll et al. ..................... | 600/407 |
| 2008/0071140 A1* | 3/2008 | Gattani et al. ................. | 600/117 |
| 2009/0062739 A1* | 3/2009 | Anderson ................ | 604/164.13 |

* cited by examiner

*Primary Examiner* — Clayton E LaBalle
*Assistant Examiner* — Warren Fenwick
(74) *Attorney, Agent, or Firm* — R. Keith Harrison

(57) ABSTRACT

An endoscope tracking system includes an endoscope, at least one endoscope tracking transmitter carried by the endoscope, a plurality of anatomy mapping transmitters, a receiver communicating with the at least one endoscope tracking transmitter and the anatomy mapping transmitters and a processor communicating with the receiver. The processor is adapted to generate an anatomical map based on input from the anatomy mapping transmitters and an endoscope tracking image based on input from the at least one endoscope tracking transmitter and superimpose the endoscope tracking image on the anatomical map.

10 Claims, 5 Drawing Sheets

ENDOSCOPE TRACKING SYSTEM AND METHOD

CROSS-REFERENCE TO RELATED APPLICATIONS

This application claims the benefit of and incorporates by reference in its entirety U.S. Provisional Application No. 61/217,672, filed Jun. 3, 2009 and entitled "ENDOSCOPE TRACKING SYSTEM AND METHOD".

FIELD

The present disclosure relates to endoscopes. More particularly, the present disclosure relates to an endoscope tracking system and method for tracking an endoscope as it is extended through a body cavity of a patient.

BACKGROUND

Endoscopes are commonly used to examine an interior body cavity such as the large intestine of a patient. A conventional endoscope typically includes an elongated, flexible shaft which terminates in a viewing window through which the interior body cavity of the patient is viewed. The shaft of the endoscope may be progressively inserted into the body cavity for examination purposes. Types of endoscopes include gastric endoscopes which are used to view the stomach and small intestine and pulmonary endoscopes which are used to view the bronchial passages of the lungs.

One of the limitations commonly encountered using conventional endoscopes is the lack of a suitable system for tracking the location of the endoscope in the body cavity of the patient during the examination procedure. Therefore, an endoscope tracking system for tracking an endoscope within a body cavity of a patient is needed.

SUMMARY

The present disclosure is generally directed to an endoscope tracking system for tracking an endoscope as it is extended through a body cavity of a patient. An illustrative embodiment of the endoscope tracking system includes an endoscope, at least one endoscope tracking transmitter carried by the endoscope, a plurality of anatomy mapping transmitters, a receiver communicating with the at least one endoscope tracking transmitter and the anatomy mapping transmitters and a processor communicating with the receiver. The processor is adapted to generate an anatomical map based on input from the anatomy mapping transmitters and an endoscope tracking image based on input from the at least one endoscope tracking transmitter and superimpose the endoscope tracking image on the anatomical map.

The present disclosure is generally directed to an endoscope tracking method. An illustrative embodiment of the endoscope tracking method includes providing an endoscope, providing at least one endoscope tracking transmitter on the endoscope, providing a plurality of anatomy mapping transmitters, placing the anatomy mapping transmitters in spatial relationship with respect to each other on a patient, generating an anatomical map of the patient using input from the anatomy mapping transmitters, generating an endoscope tracking image using input from the at least one endoscope tracking transmitter, inserting the endoscope into the patient and superimposing the endoscope tracking image on the anatomical map.

BRIEF DESCRIPTION OF THE DRAWINGS

The disclosure will now be made, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to implement the disclosure and are not intended to limit the scope of the claims. Furthermore, there is no intention to be bound by any expressed or implied theory presented in the preceding technical field, background, brief summary or the following detailed description.

Figure 2:
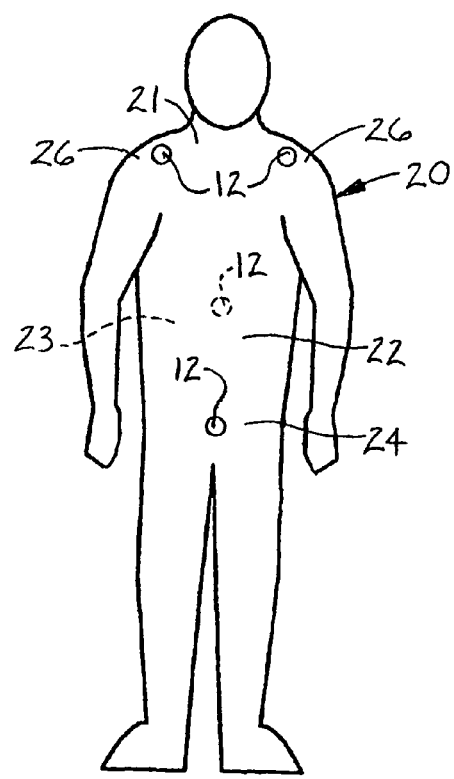
FIG. 2 is a front view of a patient, with multiple anatomy mapping transmitters placed in spatial relationship with respect to each other on the patient in implementation of an illustrative embodiment of the endoscope tracking system.
Figure 3:
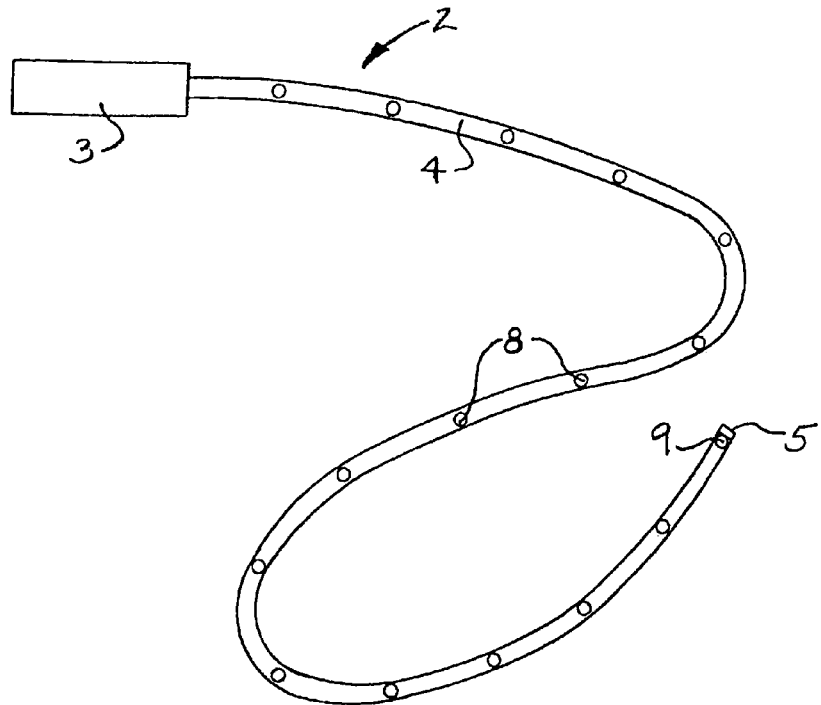
FIG. 3 is a top view of an endoscope with multiple endoscope tracking transmitters provided on an endoscope shaft of the endoscope in implementation of an illustrative embodiment of the endoscope tracking system.
Figure 4:
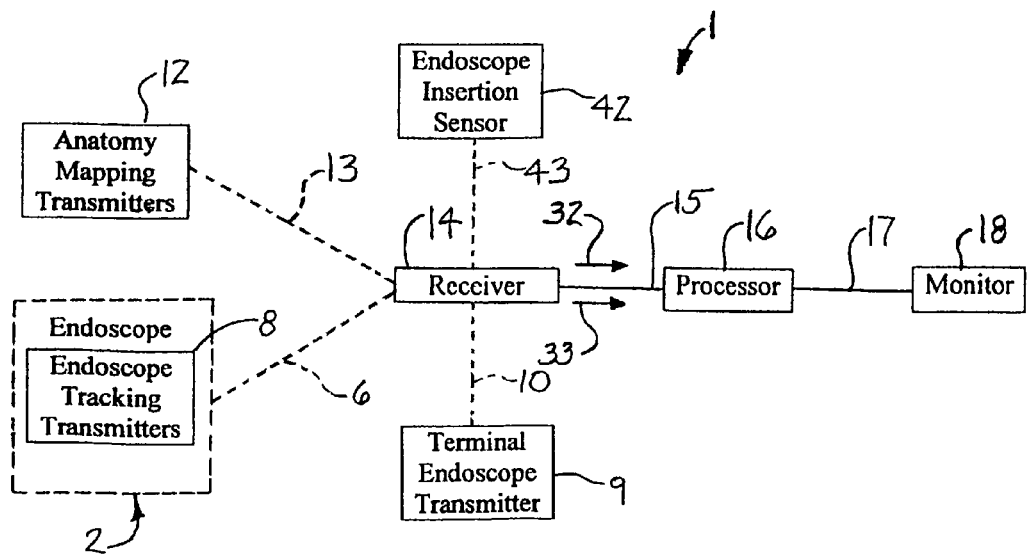
FIG. 4 is a block diagram of an illustrative embodiment of the endoscope tracking system.

Referring initially to FIGS. 1-8 of the drawings, an illustrative embodiment of the endoscope tracking system, hereinafter system, is generally indicated by reference numeral 1 in FIG. 4. As will be hereinafter described, the system 1 is adapted to generate and display an anatomical map 28 (FIGS. 6-8) of anatomical region or area of a patient 20 (FIGS. 1 and 2) such as on a monitor screen 19 (FIGS. 6-8) of a monitor 18. The anatomical map 28 may be that of the abdomen or any other anatomical region or area of the patient 20 which is to undergo medical examination in implementation of the system 1. The system 1 is further adapted to generate and display an endoscope tracking image 29 (FIGS. 6-8) and superimpose the endoscope tracking image 29 on the anatomical map 28 which is displayed on the monitor screen 19. Accordingly, as will be hereinafter described, the system 1 facilitates tracking of the endoscope 2 within the anatomical area or region in the patient 20 which is being examined as the endoscope 2 is inserted through an interior body cavity such as the large intestine 25 (FIG. 5), for example and without limitation, of the patient 20 during a medical examination procedure carried out in the interior body cavity of the patient 20.

As illustrated in FIG. 3, the endoscope 2 of the system 1 may have a conventional design and include an endoscope handle 3 from which extends an elongated, flexible endoscope shaft 4 having an endoscope working end 5. The endoscope working end 5 of the endoscope shaft 4 may include a lens (not illustrated) through which an operator (not illustrated) of the endoscope 2 views an examination field (not illustrated) inside the patient 20 as the endoscope shaft 4 is inserted through an interior body cavity such as the large intestine 25 (FIG. 5), for example and without limitation, of the patient 20. The endoscope working end 5 may also include a lens cleaning nozzle (not illustrated) through which lens cleaning fluid (not illustrated) can be ejected against the lens to rinse and clean the lens. The endoscope working end 5 may also include an instrument opening (not illustrated) through which a surgical instrument (not illustrated) may be extended to implement surgical procedures in the patient 20.

As illustrated in FIG. 3, at least one endoscope tracking transmitter 8 may be provided on the endoscope shaft 4 of the endoscope 2. Multiple endoscope tracking transmitters 8 may be provided at a selected spacing with respect to each other on the endoscope shaft 4 of the endoscope 2. In some embodiments, the endoscope tracking transmitters 8 may be provided at a spacing of 5 cm with respect to each other along the endoscope shaft 4 generally from the endoscope handle 3 to the endoscope working end 5 of the endoscope shaft 4. However, any number of endoscope tracking transmitters 8 may be provided in any desired spacing on the endoscope shaft 4 depending on the desired resolution of the endoscope tracking image 29. In some embodiments, the endoscope tracking transmitters 8 may be provided on the exterior surface of the endoscope shaft 4. In other embodiments, the endoscope tracking transmitters 8 may be embedded or encased in the endoscope shaft 4 according to the knowledge of those skilled in the art.

As illustrated in FIG. 4, the endoscope tracking transmitters 8 on the endoscope shaft 4 of the endoscope 2 may be adapted to emit wireless transmissions 6 each of which may be an RF (radio frequency) transmission, for example and without limitation. Multiple anatomy mapping transmitters 12 are adapted for spatial or three-dimensional placement on the selected anatomical area or region of the patient 20, as will be hereinafter described. The anatomy mapping transmitters 12 are adapted to emit wireless transmissions 13 each of which may be an RF (radio frequency) transmission, for example and without limitation. At least one receiver 14 (hereinafter receiver 14) is adapted to receive the wireless transmissions 6 emitted by the respective endoscope tracking transmitters 8 on the endoscope 2 and the wireless transmissions 13 emitted by the respective anatomy mapping transmitters 12 placed on the patient 20. A processor 16 may interface with the receiver 14 via a processor communication link 15. A monitor 18, having a monitor screen 19 (FIGS. 6-8), may interface with the processor 16 via a monitor communication link 17.

The receiver 14 may be adapted to discriminate among the relative spatial positions of the anatomy mapping transmitters 12 with respect to each other based on the directions from which the wireless transmissions 13 are received, the signal strengths of the wireless transmissions 13 and/or other parameters of the wireless transmissions 13 emitted by the respective anatomy mapping transmitters 12. In some embodiments, the wireless transmissions 13 emitted by the respective anatomy mapping transmitters 12 may have different frequencies to further distinguish the spatial positions of the respective anatomy mapping transmitters 12 relative to each other on the patient 20. The receiver 14 may be adapted to transmit anatomy mapping signals 32 which correspond to the relative spatial positions of the anatomy mapping transmitters 12, as indicated by the wireless transmissions 13, to the processor 16. Based on the relative spatial positions of the anatomy mapping transmitters 12 with respect to each other, the processor 16 may be programmed to generate a three-dimensional anatomical map 28 (FIGS. 6-8) of the anatomical area or region of the patient 20 on which the anatomy mapping transmitters 12 are placed. The processor 16 may be further programmed to display the anatomical map 28 on the monitor screen 19 of the monitor 18, as illustrated in FIGS. 6-8.

The receiver 14 may be adapted to discriminate among the relative spatial positions of the endoscope transmitters 8 with respect to each other and with respect to the anatomy mapping transmitters 12 based on the directions from which the wireless transmissions 6 are received, the signal strengths of the wireless transmissions 6 and/or other parameters of the wireless transmissions 6 emitted by the respective endoscope tracking transmitters 8. In some embodiments, the wireless transmissions 6 emitted by the respective endoscope tracking transmitters 8 may have different frequencies. The receiver 14 may be adapted to transmit endoscope tracking signals 33 which correspond to the relative spatial positions of the wireless transmissions 6 emitted by the respective endoscope tracking transmitters 8, to the processor 16. Based on the relative spatial positions of the endoscope tracking transmitters 8 with respect to each other, the processor 16 may be adapted to generate a three-dimensional endoscope tracking image 29 (FIGS. 6-8) of the endoscope shaft 4 of the endoscope 2.

In implementation of the system 1, which will be hereinafter further described, the endoscope shaft 4 of the endoscope 2 may be inserted into an interior body cavity which is contained within the anatomical region or area of the patient 20 on which the anatomy mapping transmitters 12 are placed. Based on the spatial positions of the endoscope tracking transmitters 8 on the endoscope shaft 4 relative to the spatial positions of the anatomy mapping transmitters 12 on the patient 20, the processor 16 may be adapted to superimpose the three-dimensional endoscope tracking image 29 of the endoscope shaft 4 on the three-dimensional anatomical map 28 displayed on the monitor screen 19 of the monitor 18, as further illustrated in FIGS. 6-8. Therefore, the three-dimensional position of the endoscope shaft 4 within the anatomical region or area of the patient 20 within which the endoscope shaft 4 is inserted may be tracked by viewing of the endoscope tracking image 29 on the anatomical map 28.

Figure 1:
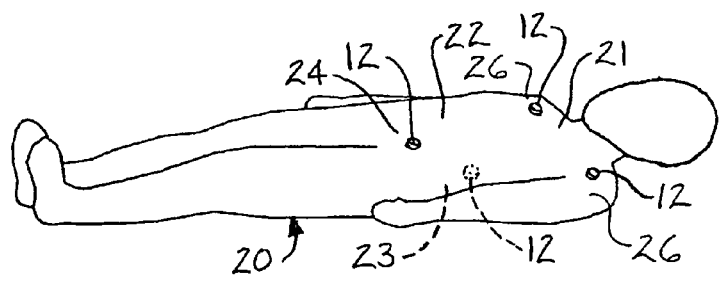
FIG. 1 is a perspective view of a patient, with multiple anatomy mapping transmitters placed in spatial relationship with respect to each other on the patient in implementation of an illustrative embodiment of the endoscope tracking system.
Figure 5:
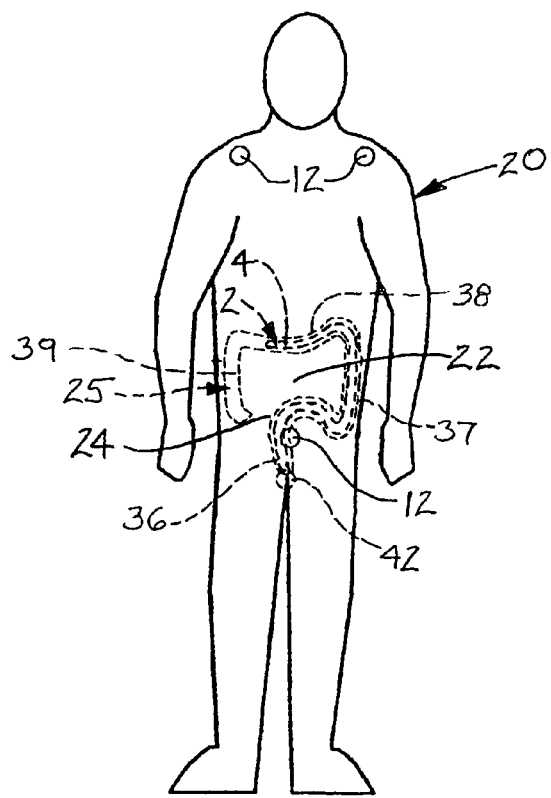
FIG. 5 is a front view of a patient, with an endoscope shaft (indicated in phantom) of the endoscope inserted into the large intestine (also indicated in phantom) of the patient in implementation of an illustrative embodiment of the endoscope tracking system.
Figure 6:
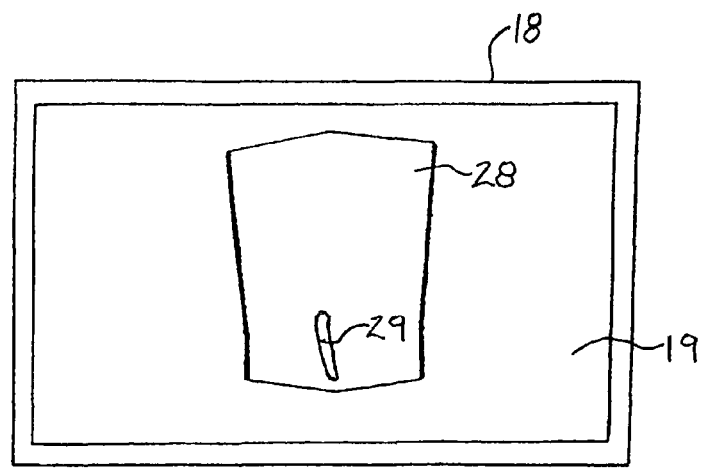
FIGS. 6-8 are front views of a monitor of an illustrative embodiment of the endoscope tracking system, with an anatomical map of the patient displayed on the monitor and an endoscope tracking image of the endoscope superimposed on the anatomical map to indicate the position of the endoscope shaft of the endoscope within the abdomen of the patient and more particularly illustrating progressive insertion of the endoscope shaft into the abdomen of the patient.
Figure 7:
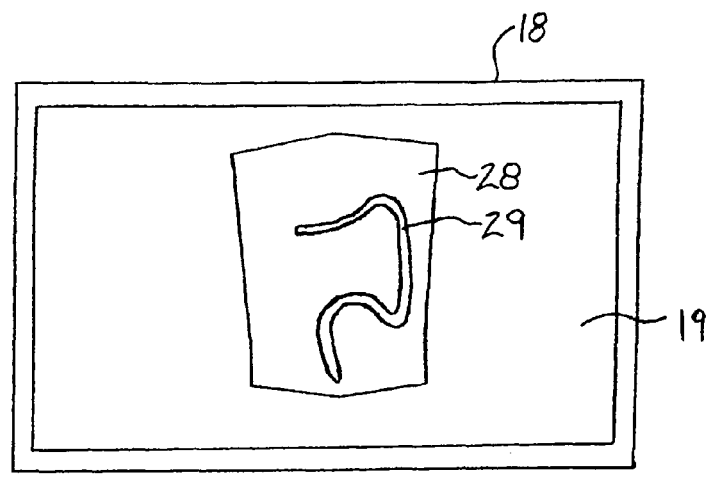
Figure 8:
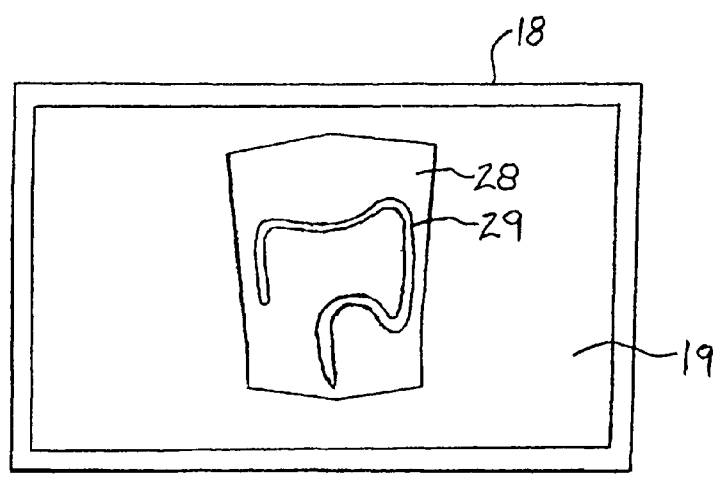

An exemplary application of the system 1 is illustrated in FIGS. 1, 2 and 5-8 of the drawings. Accordingly, in some applications the system 1 may be operated to track the progress of the endoscope shaft 4 of the endoscope 2 as the endoscope shaft 4 is inserted through the large intestine 25 (FIG. 5) of a patient 20 throughout an endoscopic examination of the large intestine 25. Therefore, the anatomical map 28 (FIGS. 6-8) which is generated by the processor 16 via input from the anatomy mapping transmitters 12 and displayed on the monitor 18 generally corresponds to an image of the abdomen 22 of the patient 20. As illustrated in FIGS. 1 and 2, at least four anatomy mapping transmitters 12 may be placed on the chest 21, the back 23 and the groin 24 of the patient 20 to generate the anatomical map 28 of the abdomen 22 of the patient 20. In some applications, a pair of spaced-apart anatomy mapping transmitters 12 may be placed on the chest 21 at the respective shoulders 26 of the patient 20. The anatomy mapping transmitters 12 may be attached to the skin of the patient 20 using suitable adhesives (not illustrated). Based on the wireless transmissions 13 (FIG. 4) which are emitted by the anatomy mapping transmitters 12 and received by the receiver 14, the processor 16 of the system 1 generates the anatomical map 28 which corresponds to the abdomen 22 of the patient 20, as was heretofore described with respect to FIG. 4, and may display the anatomical map 28 on the monitor screen 19 of the monitor 18, as illustrated in FIGS. 6-8.

Next, the endoscope shaft 4 is inserted through the anus (not illustrated) into the large intestine 25 (FIG. 4) of the patient 20, as illustrated in FIG. 5. Based on the wireless transmissions 6 which are emitted by the endoscope tracking transmitters 8 on the endoscope shaft 4 of the endoscope 2 and received by the receiver 14, the processor 16 of the system 1 generates the endoscope tracking image 29 which corresponds to the endoscope shaft 4 of the endoscope 2, as was heretofore described with respect to FIG. 4. The processor 16 superimposes the endoscope tracking image 29 on the anatomical map 28 which is displayed on monitor screen 19 of the monitor 18, as illustrated in FIGS. 6-8. As further illustrated in FIGS. 6-8, the length, position and trajectory of the endoscope tracking image 29 on the anatomical map 28 may correspond in real time to the length, position and trajectory of the endoscope shaft 4 as it is extended into the large intestine 25 of the patient 20 during the endoscopic examination of the large intestine 25. Therefore, in FIG. 6, the endoscope tracking image 29 indicates the presence of the endoscope shaft 4 in the rectum 36 (FIG. 5) of the large intestine 25. In FIG. 7, the endoscope tracking image 29 indicates that the endoscope shaft 4 has been extended through the descending colon 37 (FIG. 5) and most of the transverse colon 38 of the large intestine 25. In FIG. 8, the endoscope tracking image 29 indicates that the endoscope shaft 4 has been extended through the transverse colon 38 (FIG. 5) and most of the ascending colon 39 of the large intestine 25. Therefore, based on the progress of the endoscope shaft 4 of the endoscope 2 through the large intestine 25 of the patient 20 as indicated by the length, position and trajectory of the endoscope tracking image 29 on the anatomical map 28, the operator (not illustrated) of the endoscope 2 can readily determine which portion of the large intestine 25 is being examined at any point in time. Upon completion of the endoscopic examination, the endoscope shaft 4 may be removed from the large intestine 25 and the anatomy mapping transmitters 12 removed from the patient 20.

In some applications of the system 1, it may be desirable to determine the length of insertion of the endoscope shaft 4 as it is extended into the large intestine 25 of the patient 20. Accordingly, an endoscope insertion sensor 42 (FIG. 5) may be placed at the anus (not illustrated) at the entry of the large intestine 25 of the patient 20. A terminal endoscope tracking transmitter 9 (FIG. 3) may be provided at the endoscope working end 5 (FIG. 3) of the endoscope shaft 4. As illustrated in FIG. 4, in some embodiments the terminal endoscope transmitter 9 and the endoscope insertion sensor 42 may be adapted to communicate with the processor 16 through the receiver 14 via a transmitter communication link 10 and a sensor communication link 43, respectively. The processor 16 (FIG. 4) may be programmed to calculate the changing distance between the terminal endoscope tracking transmitter 9 and the endoscope insertion sensor 42 as the endoscope shaft 4 is progressively inserted into the large intestine 25. The processor 16 may be further programmed to display the calculated distance between the terminal endoscope transmitter 9 and the endoscope insertion sensor 42 on the monitor screen 19 of the monitor 18. In some applications, the endoscope working end 5 of the endoscope shaft 4 may be calibrated as it enters the anus (not illustrated) of the patient 20 and the length of insertion of the endoscope shaft 4 into the large intestine 25 measured as the endoscope shaft 4 is progressively inserted into the large intestine 25.

Figure 9:
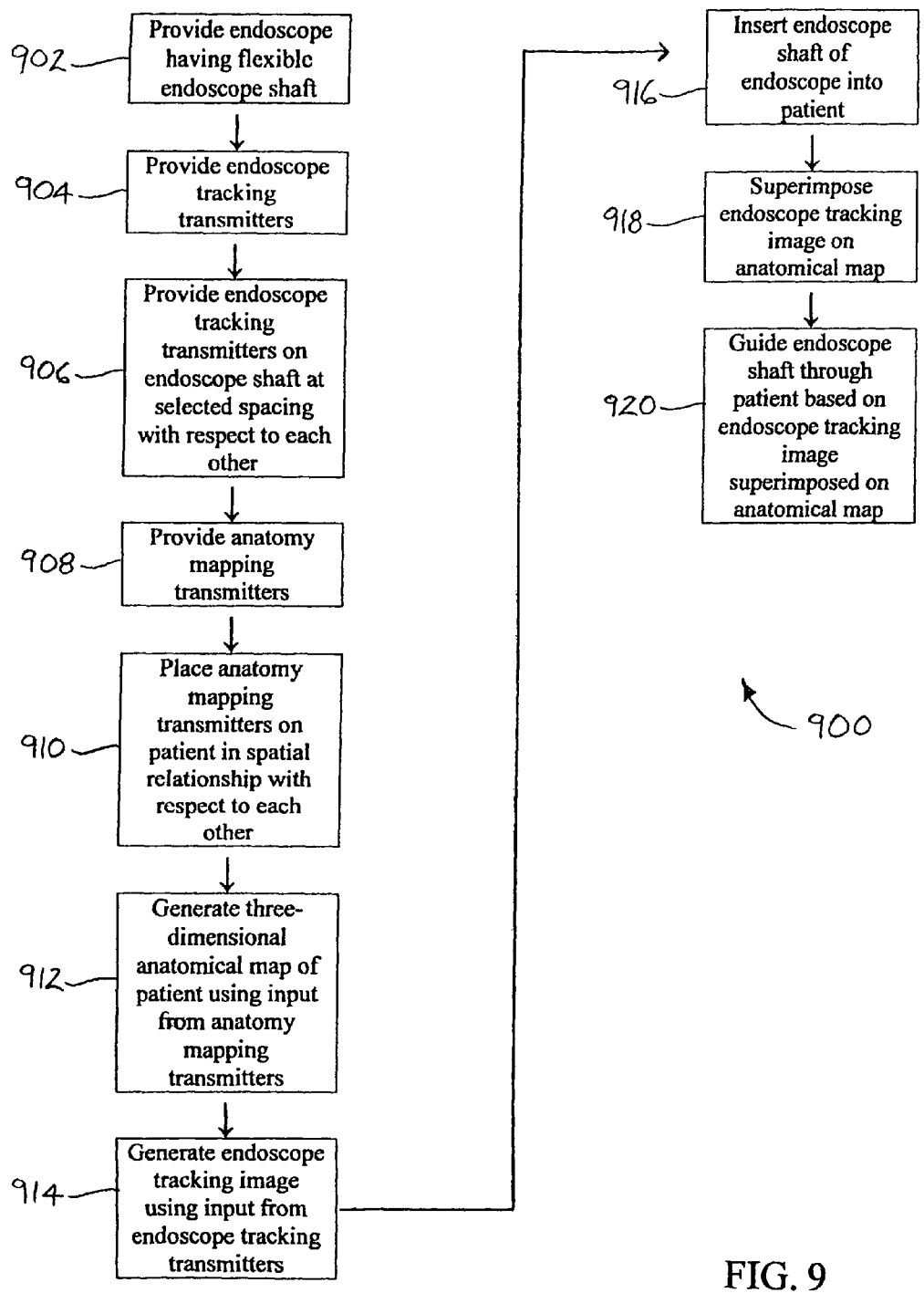
FIG. 9 is a flow diagram of an illustrative embodiment of the endoscope tracking method.

Referring next to FIG. 9 of the drawings, a flow diagram 900 of an illustrative embodiment of the endoscope tracking method is illustrated. In block 902, an endoscope having a flexible endoscope shaft is provided. In block 904, endoscope tracking transmitters are provided. In block 906, the endoscope tracking transmitters are provided on the endoscope shaft at a selected spacing with respect to each other. In block 908, anatomy mapping transmitters are provided. In block 910, the anatomy mapping transmitters are placed on a patient in spatial relationship with respect to each other. In block 912, a three-dimensional anatomical map of an anatomical region or area of the patient is generated using input from the anatomy mapping transmitters. In block 914, an endoscope tracking image is generated using input from the endoscope tracking transmitters. In block 916, the endoscope shaft of the endoscope is inserted into the patient. In block 918, the endoscope tracking image is superimposed on the anatomical map. In block 920, the endoscope shaft of the endoscope may be guided through the patient based on the endoscope tracking image superimposed on the anatomical map.

It is to be understood that any suitable technology which is known by those skilled in the art can be used to formulate the anatomical map 28 (FIGS. 6-8) and track the position and trajectory of the endoscope shaft 4 of the endoscope 2 in the anatomical region of the patient 20. For example and without limitation, in some embodiments, GPS technology may be used to track the position of the endoscope shaft 4 as it is inserted through the interior body cavity of the patient 20.

While various illustrative embodiments have been described above, it will be recognized and understood that various modifications can be made and the appended claims are intended to cover all such modifications which may fall within the spirit and scope of the disclosure.

What is claimed is:

1. An endoscope tracking system, comprising:
   an endoscope;
   at least one endoscope tracking transmitter carried by said endoscope;
   a plurality of anatomy mapping transmitters;
   a receiver communicating with said at least one endoscope tracking transmitter and said anatomy mapping transmitters;
   a processor communicating with said receiver; and
   wherein said processor is adapted to generate an anatomical map based on input from said anatomy mapping transmitters and an endoscope tracking image based on input from said at least one endoscope tracking transmitter and superimpose said endoscope tracking image on said anatomical map.

2. The system of claim 1 wherein said endoscope comprises an endoscope handle and an elongated, flexible endoscope shaft extending from said endoscope handle and wherein said at least one endoscope tracking transmitter is provided on said endoscope shaft.

3. The system of claim 1 further comprising a monitor having a monitor screen and wherein said processor is adapted to display said anatomical map and said endoscope tracking image on said monitor screen of said monitor.

4. The system of claim 1 further comprising an endoscope insertion sensor communicating with said processor and a terminal endoscope tracking transmitter provided on said endoscope and communicating with said processor.

5. The system of claim 1 wherein said at least one endoscope tracking transmitter comprises a plurality of endoscope tracking transmitters carried by said endoscope in spaced-apart relationship with respect to each other.

6. An endoscope tracking method, comprising:
providing an endoscope;
providing at least one endoscope tracking transmitter on said endoscope;
providing a plurality of anatomy mapping transmitters;
placing said anatomy mapping transmitters in spatial relationship with respect to each other on a patient;
generating an anatomical map of said patient using input from said anatomy mapping transmitters;
generating an endoscope tracking image using input from said at least one endoscope tracking transmitter;
inserting said endoscope into said patient; and
superimposing said endoscope tracking image on said anatomical map.

7. The method of claim 6 wherein said providing an endoscope comprises providing an endoscope having an endoscope handle and an elongated, flexible endoscope shaft extending from said endoscope handle, and wherein said providing at least one endoscope tracking transmitter on said endoscope comprises providing a plurality of spaced-apart endoscope tracking transmitters on said endoscope shaft.

8. The method of claim 6 wherein said generating an anatomical map of said patient comprises generating an anatomical map of an abdominal region of said patient and wherein said inserting said endoscope into said patient comprises inserting said endoscope into a large intestine of said patient.

9. The method of claim 6 further comprising providing calculating a length of insertion of said endoscope into said patient.

10. The method of claim 9 wherein said calculating a length of insertion of said endoscope into said patient comprises providing a terminal endoscope tracking transmitter on said endoscope, providing an endoscope insertion sensor on said patient and calculating a distance between said terminal endoscope tracking transmitter and said endoscope insertion sensor.

* * * * *